US010087411B1

(12) United States Patent
Hamrick

(10) Patent No.: US 10,087,411 B1
(45) Date of Patent: Oct. 2, 2018

(54) METHODS AND APPARATUS FOR SEPARATING ETHANOL FROM FERMENTED BIOMASS

(71) Applicant: Edward Brian Hamrick, Sunny Isles Beach, FL (US)

(72) Inventor: Edward Brian Hamrick, Sunny Isles Beach, FL (US)

(*) Notice: Subject to any disclaimer, the term of this patent is extended or adjusted under 35 U.S.C. 154(b) by 0 days.

(21) Appl. No.: 15/898,744

(22) Filed: Feb. 19, 2018

Related U.S. Application Data

(60) Provisional application No. 62/478,619, filed on Mar. 30, 2017.

(51) Int. Cl.
*C12M 1/00* (2006.01)
*B01D 3/00* (2006.01)
*B01D 3/14* (2006.01)
*B01D 3/32* (2006.01)
*B01D 3/38* (2006.01)
*B01D 5/00* (2006.01)
*C07C 29/80* (2006.01)
*C07C 31/08* (2006.01)
*C12P 7/06* (2006.01)
*F16L 9/12* (2006.01)

(52) U.S. Cl.
CPC ............ *C12M 47/10* (2013.01); *B01D 3/002* (2013.01); *B01D 3/146* (2013.01); *B01D 3/32* (2013.01); *B01D 3/38* (2013.01); *B01D 5/006* (2013.01); *B01D 5/0087* (2013.01); *C07C 29/80* (2013.01); *C07C 31/08* (2013.01); *C12P 7/06* (2013.01); *F16L 9/12* (2013.01)

(58) Field of Classification Search
CPC .......... C12M 47/10; B01D 3/00; B01D 3/002; B01D 3/38; B01D 3/146; B01D 5/006; B01D 5/0087; C07C 31/08; C07C 29/80; C12P 7/06
See application file for complete search history.

(56) References Cited

U.S. PATENT DOCUMENTS

| 4,634,519 A | * | 1/1987 | Danzik | ................... C10G 21/12 208/263 |
| 4,952,504 A | * | 8/1990 | Pavilon | ...................... C12P 7/06 426/49 |
| 2002/0016502 A1 | * | 2/2002 | Kanno | .................. C12P 13/005 562/443 |

* cited by examiner

*Primary Examiner* — Brian A McCaig
(74) *Attorney, Agent, or Firm* — O'Connor & Company; Ryan P. O'Connor

(57) ABSTRACT

A method for separating ethanol from fermented biomass is provided. Fermented biomass that is rich in ethanol is used directly as packing material in a distillation column, and a small amount of water at the bottom of the column is used to efficiently transfer heat to the biomass at the bottom of the column. The fermented biomass packing has a high ratio of surface area to volume, making an efficient packing material. As vapor condenses on the biomass, diffusion of ethanol/water vapor from the body of the biomass enriches the ethanol concentration at the surface of the biomass. Droplets containing lower concentrations of ethanol drip downwards from the biomass, and vapors containing higher concentrations of ethanol rise upwards from the biomass, resulting in a higher concentration of ethanol at the top of the column than was initially in the biomass.

20 Claims, 1 Drawing Sheet

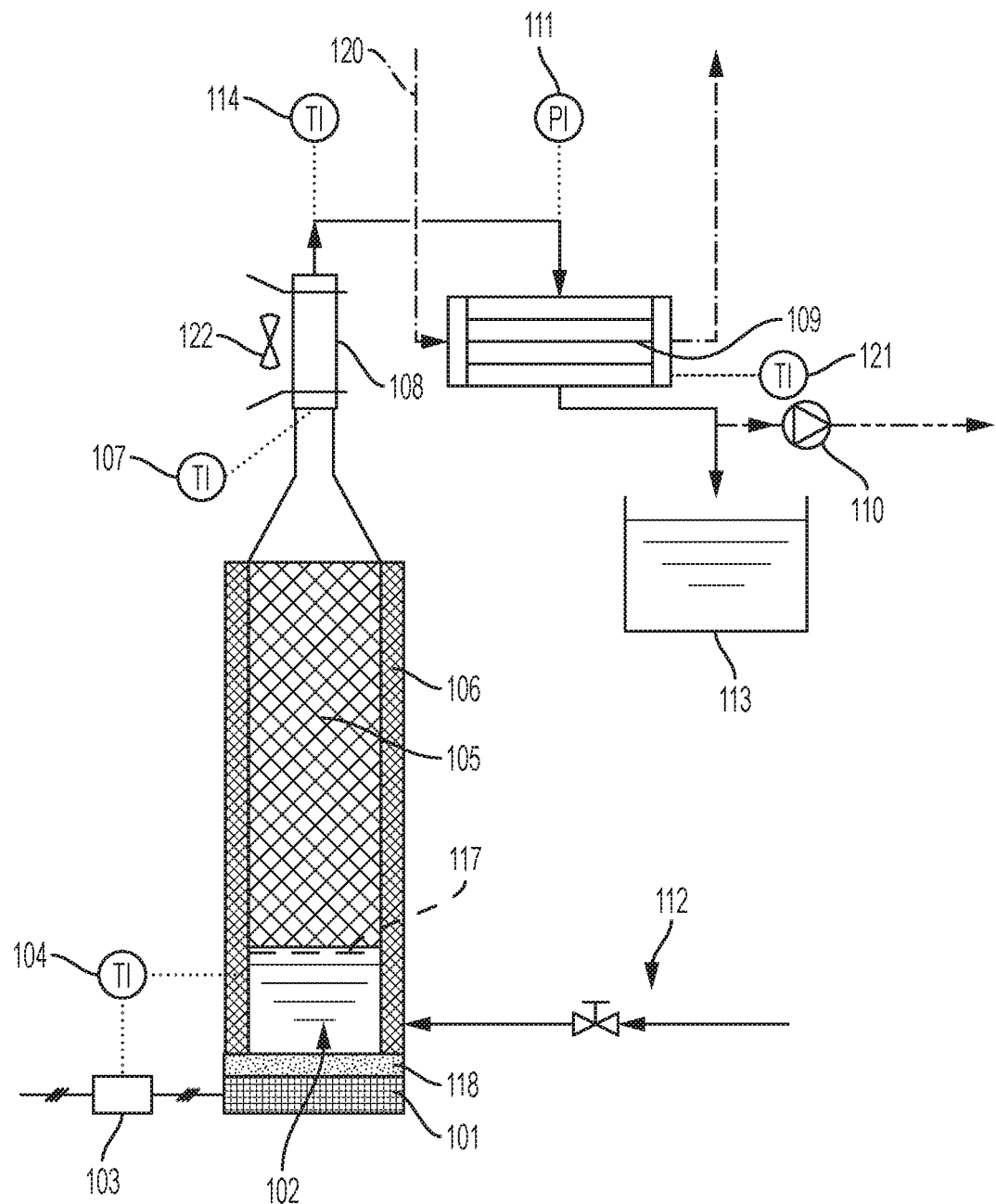

METHODS AND APPARATUS FOR SEPARATING ETHANOL FROM FERMENTED BIOMASS

PRIORITY DATA

This patent application is a non-provisional application with priority to U.S. Provisional Patent App. No. 62/478,619, filed on Mar. 30, 2017, which is hereby incorporated by reference herein.

FIELD OF THE INVENTION

The present invention pertains to processes and apparatus for separating ethanol from fermented biomass.

BACKGROUND OF THE INVENTION

There are many useful techniques for fermenting biomass to produce an ethanol-rich biomass. This is commonly referred to as "solid-state fermentation".

U.S. Pat. No. 4,490,469 describes a method for production of ethanol by fermentation. This patent teaches crushing or pulping biomass to a pulp size less than 10 mm, optionally saccharifying the pulp with acid or enzymes, mixing a yeast suspension with the pulp, waiting for fermentation to complete, and then separating ethanol by pressing or squeezing the liquid from the pulp to produce an ethanol-rich liquid.

U.S. Pat. No. 9,428,772 describes methods and systems for producing fermentation products from carbohydrate-rich substrates. This patent teaches infusing hydrolysis catalysts and fermentation organisms into lignocellulosic biomass using vacuum cycles, waiting for fermentation to complete, and separating ethanol by vacuum stripping.

U.S. Pat. No. 9,499,839 describes methods for fermenting carbohydrate-rich crops. This patent teaches infusing fermentation organisms into sugar-rich biomass, draining excess liquid from the biomass, waiting for fermentation to complete, and separating ethanol by either vacuum stripping or crushing.

U.S. Pat. No. 9,631,209 describes methods for fermenting stalks of the Poaceae family. This patent teaches crushing stalks between rollers while submerged in water containing yeast, draining excess liquid from the stalks, waiting for fermentation to complete, and separating ethanol by either vacuum stripping or crushing.

These and many other solid-state fermentation methods for producing ethanol all have the disadvantage that crushing, pressing, or squeezing generally recovers only about 50% of the ethanol from the biomass, and vacuum stripping is not very useful because the ethanol produced generally contains only about 30% to 40% alcohol by volume (ABV).

While there are many countries where there is a robust market for potable ethanol at 30% to 40% ABV (e.g., cachaca in Brazil, country liquor in India, baijiu in China, and vodka in Russia), there is an even bigger market for using ethanol in generators, in internal combustion engines, and for cooking.

Those skilled in the art will recognize that ethanol at 75% ABV is the minimum concentration required to fire a boiler. Ethanol at 85% ABV is generally the minimum concentration required to run a generator or an internal combustion engine. A fuel-injection system requires at least 92.5% ABV and preferably 96% ethanol ABV. While ethanol at 50% ABV will ignite, ethanol at 60% to 65% ABV is the minimum concentration necessary to support a stable flame for cooking, and ethanol at 80% ABV is necessary to obtain a robust flame for cooking.

The most widely used methods of producing ethanol concentrations above 80% ABV employ distillation columns. This generally starts with a liquid containing 5 vol % to 40 vol % ethanol, boiling it either at atmospheric pressure or reduced pressure, and using a distillation column to produce higher concentrations of ethanol.

Those skilled in the art will recognize that there are two types of distillation columns, those that use trays and those that use column packing, and two operating modes of distillation columns (batch and continuous).

SUMMARY OF THE INVENTION

Some variations provide a method for separating ethanol from fermented biomass, the method comprising the steps of:

(a) providing an ethanol-rich fermented biomass;

(b) packing the ethanol-rich fermented biomass into a vertical distillation column;

(c) adding water to the bottom of the vertical distillation column;

(d) heating the bottom of the vertical distillation column to boil the water, thereby producing a bottom vapor;

(e) cooling the top of the vertical distillation column to condense a top vapor, thereby producing an ethanol-rich top liquid; and (f) reintroducing a fraction of the ethanol-rich top liquid to the top of the vertical distillation column, wherein steps (d) through (f) are performed simultaneously.

In some embodiments, the ethanol-rich fermented biomass is selected from the group consisting of fermented softwood chips, fermented stalks from the Poaceae family, fermented sugar beets, fermented potatoes, fermented sweet potatoes, fermented cassava tubers, and combinations thereof In certain embodiments, the vertical distillation column is a metal drum or a metal bin. In certain embodiments, the vertical distillation column is a corrugated HDPE pipe with a metal bottom in a vertical orientation.

In some embodiments, step (c) comprises continuously or intermittently introducing external water to the vertical distillation column.

In some embodiments, heat is applied in step (d) using a method selected from the group consisting of thermal energy, induction heating, steam, and combinations thereof.

In some embodiments, cooling in step (e) is applied using a method selected from air cooling, water cooling, or a combination thereof.

In some embodiments, step (f) is performed using a dephlegmator.

Steps (d) through (f) may be performed at a pressure less than 100 kPa, for example.

In some embodiments, step (c) is performed simultaneously with steps (d) through (f).

Other variations of the invention provide an apparatus for separating a fermentation product (e.g., ethanol) from fermented biomass, the apparatus comprising:

(a) a vertical distillation column containing fermented biomass as distillation packing, wherein the fermented biomass includes a fermentation product;

(b) a water reservoir either (i) contained within the vertical distillation column or (ii) physically isolated from but in flow communication with the vertical distillation column;

(c) heating means at the bottom of the vertical distillation column;

(d) cooling means at the top of the vertical distillation column; and (e) reflux means to reintroduce cooled liquid to the top of the vertical distillation column.

In certain embodiments, the vertical distillation column is a metal drum or a metal bin. In certain embodiments, the vertical distillation column is a corrugated HDPE pipe with a metal bottom in a vertical orientation.

In some embodiments, the water reservoir is contained within the vertical distillation column, at or near the bottom of the vertical distillation column. The apparatus may further comprise means to introduce external water to the vertical distillation column. In certain embodiments, the water reservoir is physically isolated from the vertical distillation column.

The heating means may be selected from the group consisting of thermal energy, induction heating, steam, and combinations thereof The cooling means may be selected from air cooling, water cooling, or a combination thereof.

In some apparatus embodiments, the reflux means is a dephlegmator.

BRIEF DESCRIPTION OF THE DRAWING

Notwithstanding any other forms which may fall within the scope of the present invention, FIG. 1 is an exemplary drawing of an apparatus implementing the method of this invention, in some embodiments.

DETAILED DESCRIPTION OF EMBODIMENTS OF THE INVENTION

The methods, processes, and systems of the present invention will be described in detail by reference to various non-limiting embodiments and figure(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The present invention is premised on a technical solution to the problem that crushing, pressing, or squeezing generally recovers only 50% of the ethanol from fermented biomass, and vacuum stripping is not very useful because the ethanol produced generally contains only about 30% to 40% alcohol by volume (ABV).

This invention is predicated, at least in part, on the technical approach of utilizing the fermented biomass itself as packing material in a distillation column.

Principles of the invention, in some variations, are demonstrated in the Examples herein. Note that while many embodiments pertaining to ethanol are described, the invention is not limited to ethanol as the fermentation product contained in the fermented biomass. Various alcohols, organic acids, hydrocarbons, and other compounds may be produced, in other embodiments.

The invention provides a method for separating ethanol from fermented biomass, the method comprising the steps of:

(a) providing an ethanol-rich fermented biomass;

(b) packing the ethanol-rich fermented biomass into a vertical column;

(c) adding water to the bottom of the vertical column;

(d) heating (e.g., by applying heat or under suitable temperatures) to the bottom of the vertical column to boil the water, producing a bottom vapor;

(e) cooling (e.g., by applying cooling or under suitable temperatures) to the top of the vertical column to condense top vapor and produce an ethanol-rich top liquid; and (f) reintroducing a fraction of the ethanol-rich top liquid to the vertical column, preferably at or near the top of the vertical column, wherein steps (d) through (f) are preferably performed simultaneously.

Those skilled in the art will recognize that this method is similar to a packed distillation column, except that (a) the packing material is or includes fermented biomass and (b) water or an aqueous solution at the bottom of the distillation column is used to transfer heat to the fermented biomass at the bottom of the distillation column.

Fermented biomass that is rich in ethanol is used as packing material in the distillation column, and a small amount of water at the bottom of the column may be used to efficiently transfer heat to the biomass at the bottom of the column. The fermented biomass packing has a high ratio of surface area to volume and therefore is an efficient packing material. As vapor condenses on the biomass, heat diffuses into the biomass, causing an ethanol/water vapor to be produced, which vapor is then expelled from the biomass through the apoplast or fibers of the biomass. This ethanol/water vapor from the body (bulk phase) of the biomass enriches the ethanol concentration at the surface of the biomass particles. Because ethanol is more volatile than water, droplets containing lower concentrations of ethanol drip downwards from the biomass, and vapor containing higher concentrations of ethanol rise upwards from the biomass. This results in a higher concentration of ethanol at the top of the column than was initially in the fermented biomass.

The diffusion of heat into the biomass takes some time. This is described in Chapter 5 of Lienhard IV, J. H., and V. Lienhard, *A Heat Transfer Textbook*, $4^{th}$ Ed., Cambridge Massachusetts (2017), which is hereby incorporated by reference herein, and referred to herein as "Leinhard". FIG. 5.8 (for cylinders, e.g. stalks) and FIG. 5.9 (for spheres, e.g. tubers and wood chips) in Leinhard give a simple way to compute how long it takes for the center of biomass to heat to the boiling point of the ethanol in the biomass. For example, a fermented sugar beet with a diameter of 0.1 m (4 in.) has a Fourier number (Fo) of 0.208 after one hour (same as in Example 5.2 in Leinhard). A fermented sugar beet with sugar of 18% by weight will have an ethanol content of about 10% ABV, which has a boiling point of about 94° C. (which in FIG. 5.9 is a dimensionless temperature of about 0.05). For condensing steam (1000 W m$^{-2}$ K$^{-1}$), the Biot number (Bi) of this sugar beet is about 83, and 1/Bi is therefore about 0.012. The top left corner of FIG. 5.9 in Leinhard shows that condensing steam will heat the center of this sugar beet to about 94° C. in about 1.5 hours.

In preferred embodiments, the fermented biomass is selected from the group consisting of fermented softwood chips, fermented stalks from the Poaceae family (e.g., sugar cane and sweet sorghum), fermented sugar beets, fermented potatoes, fermented sweet potatoes, fermented cassava tubers, and combinations thereof. These are the most commonly grown carbohydrate-rich crops, but this list is not exhaustive and the principles of the invention may be applied to other biomass feedstocks. The geometry of the fermented biomass may vary, such as spheres, rods, tubes, fibers, plates, mats, chips, random orientations, or a combination thereof. Optionally, the fermented biomass is pressed into selected distillation column packing geometries, but this is by no means necessary.

The fermented biomass is typically obtained from solid-state fermentation of starting biomass, using one or more suitable microorganisms, to at least partially ferment sugars or sugar polymers into fermentation products still contained within the biomass. Solid-state fermentation is a cultivation technique in which microorganisms ferment sugars to products (such as ethanol) under controlled conditions on moist solid particles, with sufficient moisture to maintain microbial growth and/or metabolism. Some embodiments employ methods as taught in U.S. Pat. Nos. 9,428,772, 9,499,839, and/or 9,631,209, which are hereby incorporated by reference herein. Those skilled in the art will recognize that there are many methods and suitable organisms for solid-state fermentation of carbohydrate-rich biomass to ethanol or other fermentation products.

Also, fermented biomass may be obtained from fermentation of biomass that may be different than solid-state fermentation. For example, submerged-liquid fermentation of biomass may be employed in which fermented biomass is then recovered (such as via filtration or centrifugation) for use in the present invention. This is less practical because fermentation products are also contained in the liquid phase, but it remains in the scope herein. The fermentation products in the liquid phase may be separately recovered and/or optionally may be fed into a distillation column as provided herein, in dilute form, for purification while utilizing the recovered fermented biomass as distillation packing.

The fermented biomass may contain various concentrations of ethanol, such as about or at least about 0.1, 0.5, 1, 2, 3, 4, 5, 6, 7, 8, 9, 10, 11, 12, 13, 14, 15 wt % or more on the basis of the total weight of fermented biomass with all components, including all solids and water.

Many types of distillation columns may be used in this invention. The simplest is to use a metal-bottomed container such as a 204 L (55 gal.) drum, or a large metal bin, or a large-diameter (>0.5 m) corrugated HDPE pipe stood on end with a metal plug at the bottom. Corrugated HDPE pipe can be advantageous in that it is inexpensive per unit volume, it is insulated, and it can sustain vacuum pressure.

In some embodiments, the vertical column is a metal drum. In some embodiments, the vertical column is a metal bin. In some preferred embodiments, the vertical column is a corrugated high-density polyethylene (HDPE) pipe with a metal bottom in a vertical orientation.

In step (c), water may be added by continuously or intermittently introducing external water to the vertical distillation column. For example, external water may be pumped into the vertical column. In some embodiments, a suitable amount of water is initially placed into the bottom of the distillation column, and additional water may or may not be required during operation of the distillation column. In certain embodiments, enough water is contained in the fermented biomass so that additional (external) water does not need to be introduced initially or continuously into the bottom of the column. In other words, when sufficient water is contained in the fermented biomass, during operation a portion of that water diffuses out of biomass particles and drops to the bottom of the column. Water is still added to the bottom of the vertical column (step (c)), but it is water initially contained in the fermented biomass. Combinations are possible. For example, an initial amount of water may be placed in the column for start-up. During operation, that water is vaporized but may be replaced, partially or completely, with water derived from the fermented biomass. If that is still insufficient, then external water may be introduced continuously or periodically into the distillation column. In some embodiments, step (c) is performed simultaneously with steps (d) through (f).

As the top liquid is removed from the top of the column, liquid water may need to be added to the bottom of the column to provide heat transfer to the fermented biomass, when the starting water content of the fermented biomass is insufficient. Otherwise, the bottom of the column may dry out and heat transfer would only be by conduction, which is far less efficient than boiling of the water at the bottom of the column.

In some embodiments, sufficient water is introduced at the bottom of the column so that the bottom never goes dry during the distillation. This water may be introduced initially in the column and/or periodically introduced during distillation. In practice, a water level of about 5% of the height of the column is typically sufficient, since water is also expelled from the biomass along with the ethanol, and this water migrates down the column while the ethanol migrates up the column. In various embodiments, a water level of about 1%, 2%, 5%, 10%, 15%, 20%, or 25% of the height of the column is employed. Preferably, the amount of water at the bottom of the column is sufficient to coat the outside of the biomass when condensing.

In preferred embodiments, the heat is applied to the column using a method selected from the group consisting of thermal energy, induction heating, steam, and combinations thereof.

Energy is the main cost of distillation, and those skilled in the art will recognize the tradeoffs of using various types of thermal energy, induction heating, and steam. If induction heating is used, the bottom of the distillation column is preferably a ferrous metal, and preferably not stainless steel.

In preferred embodiments, the cooling is applied using a method selected from air cooling, water cooling, or a combination thereof. In various embodiments, cooling may be applied generally using gas cooling, liquid cooling, or combined gas/liquid cooling. Liquid coolants other than water are known to those skilled in the art.

Air cooling of the condenser requires a larger area than water cooling, but cool air is often more economical. Those skilled in the art will recognize the tradeoffs of using different types of condenser cooling.

In preferred embodiments, step (f) is performed using a dephlegmator. A dephlegmator is a device arranged for the partial condensation of a multicomponent vapor stream. The vapor stream flows vertically upwards and the condensate (condensed vapor) runs back down under the influence of gravity. Dephlegmators provide a good means to combine reflux with even redistribution of reflux to the top of the column. One preferred embodiment, which is simple and inexpensive, is an air-cooled flat metal plate with holes for the vapor to escape the distillation column.

In some embodiments, step (f) reintroduces ethanol-rich top liquid at the top of the vertical distillation column. Alternatively, or additionally, step (f) may reintroduce ethanol-rich top liquid near the top of the vertical distillation column, but not at the top, such as about 50%, 60%, 70%, 90%, 90%, or 95% of the height of the vertical distillation column (100% height being the top of the vertical distillation column itself but not including the dephlegmator or other devices above the column or downstream of the top of the column).

The fraction of ethanol-rich top liquid that may be reintroduced to the vertical distillation column may vary widely, such as a weight ratio from about 0.01 to about 0.99. In various embodiments, the weight ratio is about 0.02, 0.05, 0.1, 0.2, 0.3, 0.4, 0.5, 0.6, 0.7, 0.8, 0.9, or 0.95. During operation, the weight ratio (fraction reintroduced to the column) may vary, due to variations in temperature or pressure, variations in concentration as ethanol is released from the fermented biomass, or randomly.

Typically, the ethanol-rich top liquid is reintroduced to the vertical distillation column in a substantially continuous manner, in the same way that ethanol is distilled from the fermented biomass substantially continuously. However, variations in time and space can happen during distillation, due to underlying thermodynamics, mass transfer, and heat transfer. In certain embodiments, ethanol-rich top liquid is reintroduced to the vertical distillation column in an intentionally intermittent manner, such as when a control scheme is used to monitor the local concentrations of ethanol.

In preferred embodiments, steps (d) through (f) are performed at an absolute pressure less than about 100 kPa (atmospheric pressure), such as about or less than about 90 kPa, 80 kPa, 70 kPa, 60 kPa, 50 kPa, 40 kPa, 30 kPa, 20 kPa, or 10 kPa.

In some embodiments, step (d) is performed at a temperature of about, or less than about, 90° C., 80° C., 70° C., 60° C., 50° C., 40° C., or 30° C.

Using pressures below atmospheric pressure allows the use of lower-temperature heat at the bottom of the distillation column. This makes it possible to use solar heat, flue gas, warm water, or other sources of lower-temperature heat for the distillation column. It also results in less heat loss to the environment through the walls of the distillation column, increasing the overall efficiency.

Fermented biomass that is rich in ethanol often contains pectin in the parenchyma tissue. Pectin degrades with heat, producing methanol, which is usually an undesired product of distillation. This is described in Diaz, Jerome V., Gordon E. Anthon, and Diane M. Barrett, "Nonenzymatic degradation of citrus pectin and pectate during prolonged heating: effects of pH, temperature, and degree of methyl esterification," *Journal of agricultural and food chemistry* 55.13 (2007): 5131-5136, which is hereby incorporated by reference herein. FIG. 3(A) therein shows that the amount of methanol produced from pectin when heating is about one-tenth as much at 75° C. as at 100° C.

An exemplary apparatus implementing the method of this invention is shown in FIG. 1. Again, the invention is not limited to ethanol is the fermentation product.

Biomass impregnated with ethanol, 105, is located inside the column 106 over a perforated plate 117. Column 106 is preferably wrapped in appropriate insulating material (not shown) although the lack of such insulation would not prevent the working of the apparatus and would impact only its energy efficiency. A perforated plate 117 prevents the biomass from contacting the water in the reservoir 102 which is kept with sufficient water through the water supply 112. The perforated plate 117 is not critical; a lack of a perforated plate would not prevent the working of the apparatus and would only slightly increase fouling of metal plate 118. At the bottom of the column 106, a metal plate 118 is disposed above a heater 101 controlled by a temperature indicator 104 and a power controller 103. The heater 101 provides heat to the reservoir 102 to vaporize the water while the metal plate 118 ensures uniform distribution of the heat. In some embodiments, the heater 101 is electric. However, other heating devices may be used, including a steam heater, a direct fired heater, a hot oil heater, or a solar heater.

In the embodiments depicted in FIG. 1, the reservoir 102 is contained within the column. In other embodiments, the reservoir is physically separated from the column with adequate means to flow water vapor from the reservoir to the column and condensate from the column to the reservoir.

As water vapor rises through the column 106, the vapor enriches with low-boiling ethanol, resulting in the biomass decreasing its ethanol content. Upon leaving the biomass 105, the ethanol-rich vapor goes through a dephlegmator 108 which cools down the vapor and, by providing partial condensation, allows further concentration of the ethanol. Temperature controllers 107 and 114 may be used to measure the temperature of the vapor leaving the biomass 105 and the temperature of the vapor leaving the dephlegmator 108, respectively. This temperature differential may be controlled by varying the cooling of the dephlegmator 108 with cooler 122. In some embodiments, the cooler 122 is an air cooler, but other cooling systems could be used, such as a water jacket or a coil with cooling liquid outside or inside the path of the flow. Vapor leaving the dephlegmator 108 is wholly condensed in condenser 109. The condenser 109 shown in this embodiment is liquid cooled. Line 120 indicates the flow of an appropriate cooling medium, but other cooling media such as forced air convention or natural air convection may be used. A vacuum pump 110 is used to control the pressure in the system. The system pressure is indicated in the pressure gauge 111. The vacuum pump may be configured to allow system operation under high vacuum or solely for the expulsion of cold incondensable gases. In some embodiments designed to operate only at ambient or near ambient temperature, the vacuum pump may be omitted. Temperature indicator 121 indicates the temperature inside the condenser 109. Ethanol-rich condensate is collected in the collection vessel 113.

A person of ordinary skill in the art will recognize that known equipment and components may be employed for the processes, methods, apparatus, and systems disclosed herein. The processes herein may be batch, continuous, semi-continuous, or pseudo-continuous.

For example, step (b) of packing the ethanol-rich fermented biomass into a vertical column may be done batchwise, followed by continuous operation of steps (d) to (f), and optionally step (c). In some commercial embodiments, step (b) is also continuous or semi-continuous, i.e. the ethanol-rich fermented biomass may be introduced into the column through a port such as near the top of the column while ethanol-depleted biomass may be withdrawn from the column through a port such as near the bottom of the column.

The throughput, or process capacity, may vary widely from small laboratory-scale units to full commercial-scale units, including any pilot, demonstration, or semi-commercial scale. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, or higher.

The overall system may be at a fixed location, or it may be made portable. The system may be constructed using modules which may be simply duplicated for practical scale-up.

Various probes may allow precise process monitoring and control across various stages of the process, up to and potentially including all stages of the process. Precise process monitoring would be expected to result in yield and efficiency improvements, both dynamically as well as over a period of time when operational history can be utilized to adjust process conditions (including pressure cycling programs). In some embodiments, a reaction probe is disposed in operable communication with a process zone. Such a reaction probe may be useful to extract liquid samples and analyze them, in order to determine extent of separation, or ethanol profile, etc. Process adjustments may be based on measurements, if deemed necessary or desirable, using well-known principles of process control (feedback, feed-forward, proportional-integral-derivative logic, etc.).

Solid, liquid, and gas streams produced or existing within the process can be independently recycled, passed to subsequent steps, or removed/purged from the process at any point.

EXAMPLES

A test apparatus was built, corresponding to the exemplary apparatus in FIG. 1. Three distillation tests were performed: the first at atmospheric pressure (101.325 kPa) with ethanol-infused wood chips, the second at atmospheric pressure with fermented sugar cane, and the third at 50 kPa pressure with ethanol infused wood cubes.

Biomass 105 in the first test was 12 mm softwood cubes infused under vacuum with a 10% ABV solution. Biomass 105 in the second test was sugar cane fermented according to the method in U.S. Pat. No. 9,631,209 (which is hereby incorporated by reference herein), cut into 25 mm lengths so it would fit in the column. Biomass 105 in the third test was 12 mm softwood cubes infused under vacuum with a 10% ABV solution.

No vacuum pump, 110, was used in the first and second tests, and a vacuum pump was used in the third test to maintain pressure gauge 111 at 50 kPa.

Column 106 was a 304 stainless steel pipe with a length of 91 cm, an inner diameter of 45 mm and an outer diameter of 51 mm and was wrapped in fiberglass mat water heater pipe insulation.

Reservoir 102 in each test initially contained 200 mL of distilled water and perforated plate 117 was not used. At the end of each test, roughly 125 mL of liquid remained in Reservoir 102.

Metal plate 118 was a 304 stainless steel plate with a surface area of 2600 cm$^2$, welded to the bottom of column 106.

Heater 101 was a 1200 W commercial hot plate, bolted to the underside of metal plate 118. Temperature indicator 104 was not used, and power controller 103 was a rheostat which was left in the full-on position during these three tests.

Dephlegmator 108 was a 9 cm length of two-wall copper tube, inner diameter 14 mm and outer diameter 20 mm.

Temperature controllers 107 and 114 were thermocouples measuring the temperature of the vapor leaving the biomass and the temperature of the vapor leaving the dephlegmator, respectively.

In the first and second tests, cooler 122 was variable-flow air pumped with a peristaltic pump to control the temperature at temperature controller 114 below 80° C. In the third test, cooler 122 was constant-flow water at a constant temperature of 60° C.

Condenser 109 was a 50 cm length of two-wall copper tube, inner diameter 20 mm and outer diameter 28 mm.

Temperature indicator 121 was maintained at 10° C.

Collection vessel 113 was a 250 mL Erlenmeyer flask, connected to the condenser with a rubber stopper such that it could be maintained under vacuum in the third test.

A solution of 800 mL distilled water and 200 mL of 50% ABV ethanol was prepared for the first and third tests. This is 10% ABV, 8.01% alcohol by weight.

In the first test, this 10% ABV solution was infused using vacuum into 200 g of bone dry softwood cubes, 12 mm on each side. After infusion, the weight was 441.8 g, so 241.8 g of 10% ABV solution was infused into the wood cubes. This was 241.8 g×8.01%=19.37 g of ethanol. After 6 hours of distillation at atmospheric pressure, 23.492 g of distillate was recovered, and the mass of 20 mL of this distillate was 16.8 g. The density was 0.84 g/cm$^3$, 86.6% ABV, 81.3% by weight, for a total of 19.09 g of ethanol recovered, or 98% recovered (with an uncertainty due to experimental error of about 5%).

In the second test, 500 g of sugar cane was infused with yeast using the method of U.S. Pat. No. 9,631,209, and fermented for 60 hours. The progress of fermentation was measured by gas produced using a MilliGascounter, type MGC-1, from Dr.-Ing. Ritter Apparatebau GmbH & Co. KG in Bochum, Germany. The amount of gas produced is measured at the milliliter resolution over the period of the fermentation. The fermentation of 3.35 g of sugar (normally sucrose) generates 1 L of gas ($CO_2$), so the amount of sugar fermented, the rate of fermentation, and the total amount of sugar fermented can be inferred by the graph of gas produced over time. 9 liters of gas were measured, meaning 30.15 g of sugar was fermented and about 15 g of ethanol was produced. 56 g of liquid was expelled from 564 g of infused sugar cane, and this expelled liquid was not used in the distillation column, so about 13.5 g of ethanol remained in the sugar cane. After 5 hours of distillation at atmospheric pressure, 12.71 g of distillate was recovered, and the mass of 10 mL of this distillate was 8.24 g. The density was 0.824 $g/cm^3$, 91.54% ABV, 87.7% by weight, for a total of 11.15 g of ethanol recovered, or 83% recovered (with an uncertainty due to experimental error of about 10%).

In the third test, a 10% ABV solution was infused using vacuum into 231 g of bone dry softwood cubes, 12 mm on each side. After infusion, the weight was 491 g, so 260 g of 10% ABV solution was infused into the wood cubes. This was 260 g×8.01%=20.83 g of ethanol. After 3.5 hours of distillation at 50 kPa pressure, 28 mL of distillate was recovered, and the mass of 20 mL of this distillate was 16.72 g, so 23.41 g of distillate was recovered. The density was 0.836 $g/cm^3$, 87.89% ethanol by volume, 82.97% ethanol by weight, for a total of 19.42 g of ethanol recovered, or 93% recovered (with an uncertainty due to experimental error of about 5%).

The results of these three tests are evidence that the method of this invention is a useful and practical way to separate ethanol from fermented biomass.

Those skilled in the art will recognize that improvements in amount of ethanol recovered and concentration of distillate can easily be accomplished by better control of temperature at the dephlegmator.

The principles of the invention may be applied to other fermentation products than ethanol, such as (but not limited to) alcohols, organic acids, hydrocarbons, and so on.

In this detailed description, reference has been made to multiple embodiments. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments and variations described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

What is claimed is:

1. A method for separating ethanol from fermented biomass, said method comprising the steps of: (a) providing an ethanol-rich fermented biomass; (b) packing a vertical column with packing consisting essentially of said ethanol-rich fermented biomass; (c) adding a liquid consisting essentially of water to the bottom of said vertical column; (d) heating the bottom of said vertical column to boil said liquid, thereby producing a bottom vapor; (e) cooling the top of said vertical column to condense a top vapor, thereby producing an ethanol-rich top liquid; and (f) reintroducing a fraction of said ethanol-rich top liquid to the top of said vertical column, wherein steps (d) through (f) are performed simultaneously.

2. The method of claim 1, wherein said ethanol-rich fermented biomass is selected from the group consisting of fermented softwood chips, fermented stalks from the Poaceae family, fermented sugar beets, fermented potatoes, fermented sweet potatoes, fermented cassava tubers, and combinations thereof.

3. The method claim 1, wherein said vertical column is a metal drum or a metal bin.

4. The method of claim 1, wherein said vertical column is a corrugated HDPE pipe with a metal bottom in a vertical orientation.

5. The method of claim 1, wherein step (c) comprises continuously or intermittently introducing external water to said vertical column.

6. The method of claim 1, wherein heat is applied in step (d) using a method selected from the group consisting of thermal energy, induction heating, steam, and combinations thereof.

7. The method of claim 1, wherein said cooling in step (e) is applied using air cooling, water cooling, or a combination thereof.

8. The method of claim 1, wherein step (f) is performed using a dephlegmator.

9. The method of claim 1, wherein steps (d) through (f) are performed at a pressure less than 100 kPa.

10. The method of claim 1, wherein step (c) is performed simultaneously with steps (d) through (f).

11. An apparatus for separating a fermentation product from fermented biomass, said apparatus comprising: (a) a vertical column containing packing consisting essentially of fermented biomass and a fermentation product within said fermented biomass; (b) a water reservoir either (i) contained within said vertical column or (ii) physically isolated from but in flow communication with said vertical column; (c) a heater disposed at the bottom of said vertical column; (d) a cooler disposed at the top of said vertical column; and (e) a reflux device to reintroduce cooled liquid to said top of said vertical column.

12. The apparatus of claim 11, wherein said vertical column is a metal drum or a metal bin.

13. The apparatus of claim 11, wherein said vertical column is a corrugated HDPE pipe with a metal bottom in a vertical orientation.

14. The apparatus of claim 11, wherein said water reservoir is contained within said vertical column, at or near the bottom of said vertical column.

15. The apparatus of claim 14, said apparatus further comprising a pump to introduce external water to said vertical column.

16. The apparatus of claim 11, wherein said water reservoir is physically isolated from said vertical column.

17. The apparatus of claim 11, wherein said heater is selected from the group consisting of an electric heater, a steam heater, a direct fired heater, a hot oil heater, an induction heater, and a solar heater.

18. The apparatus of claim 11, wherein said cooler is selected from an air cooler, a water cooler, or a combination thereof.

19. The apparatus of claim 11, wherein said reflux device is a dephlegmator.

20. The apparatus of claim 11, wherein said fermentation product contained within said packing is ethanol.

\* \* \* \* \*